United States Patent [19]
Dowd et al.

[11] Patent Number: 5,377,677
[45] Date of Patent: Jan. 3, 1995

[54] PACKAGING SYSTEM FOR A FETAL ELECTRODE

[75] Inventors: Edward Dowd, Mallorytown; Joseph O'Neill, Gananoque, both of Canada; David M. DiSabito, Clarence, N.Y.; James R. Hubbard, Lumberton; Cleatis A. Eichelberger, Delran, both of N.J.

[73] Assignee: Graphic Controls Corporation, Buffalo, N.Y.

[21] Appl. No.: 126,222

[22] Filed: Sep. 23, 1993

Related U.S. Application Data

[63] Continuation-in-part of Ser. No. 97,983, Jul. 27, 1993, abandoned, which is a continuation-in-part of Ser. No. 959,990, Oct. 13, 1992, abandoned.

[51] Int. Cl.$^6$ .......................................... A61B 5/0448
[52] U.S. Cl. ............................ 128/642; 607/127; 607/116
[58] Field of Search ..................... 128/639, 642; 607/115–116, 139, 147, 149, 902, 126–127

[56] References Cited

U.S. PATENT DOCUMENTS

| | | |
|---|---|---|
| Re. 28,990 | 10/1976 | Hon et al. . |
| 3,827,428 | 8/1974 | Hon et al. . |
| 3,910,271 | 10/1975 | Neward . |
| 3,986,497 | 10/1976 | Dali . |
| 4,080,961 | 3/1978 | Eaton . |
| 4,149,528 | 4/1979 | Murphy . |
| 4,254,764 | 3/1981 | Neward . |
| 4,301,806 | 11/1981 | Helfer . |
| 4,320,764 | 3/1982 | Hon . |
| 4,321,931 | 3/1982 | Hon . |
| 4,501,276 | 2/1985 | Lombardi . |
| 4,577,635 | 3/1986 | Meredith . |
| 4,644,957 | 2/1987 | Ricciardelli et al. . |
| 4,911,657 | 3/1990 | Berlin . |
| 4,913,151 | 4/1990 | Harui et al. . |
| 4,934,371 | 6/1990 | Malis et al. . |
| 4,951,680 | 8/1990 | Kirk et al. . |
| 5,012,811 | 5/1991 | Malis et al. . |
| 5,046,965 | 9/1991 | Neese et al. . |
| 5,062,426 | 11/1991 | Ulbrich et al. . |
| 5,168,876 | 12/1992 | Quedens et al. . |
| 5,199,432 | 4/1993 | Quendens et al. . |
| 5,205,288 | 4/1993 | Quedens et al. . |
| 5,215,090 | 6/1993 | Hon et al. . |

FOREIGN PATENT DOCUMENTS

| | | |
|---|---|---|
| 0258961 | 3/1988 | European Pat. Off. . |
| 0484107A1 | 5/1992 | European Pat. Off. . |

OTHER PUBLICATIONS

"Medi–Trace Disposable Patient Monitoring Systems", publication of Graphic Controls Corporation, Ontario, Canada, Aug. 1990.
Packaging for Spiral Electrode Manufactured by LIT Ltd, for advanced Medical Systems, Inc., Publicly Available at least since Feb. 1992.
Medi–Trace Fetal ECG–Electrode, Graphic Controls Canada Limited, (Jun. 1984).
European Search Report for Corresponding Application No. 93308131.7, dated Feb. 11, 1994.

Primary Examiner—Angela D. Sykes
Attorney, Agent, or Firm—Ratner & Prestia

[57] ABSTRACT

A packaging system for a fetal electrode assembly. The assembly includes an electrode which can be attached to a fetus. The electrode is coupled to an electrode wire. The electrode wire extends through a drive tube and terminates in a connector end. A flexible guide tube receives the drive tube. The packaging system includes a handle and a clip. The handle is attached to the rearward end of the drive tube. The handle has a forward section which detachably mounts inside the rearward end of the guide tube. The handle also has a passage for receiving the connector end and a slot for securing the electrode wire when the electrode is not in use. The electrode projects from the forward end of the guide tube when the forward section of the handle is mounted inside the rearward end of the guide tube. The clip has a head mounted to the handle and a tail which is wedged between the rearward end of the guide tube and the rearward end of the drive tube to secure the handle when the forward section of the handle is not mounted inside the rearward end of the guide tube. The electrode is retracted into and protected by the guide tube when the handle is secured by the clip.

28 Claims, 10 Drawing Sheets

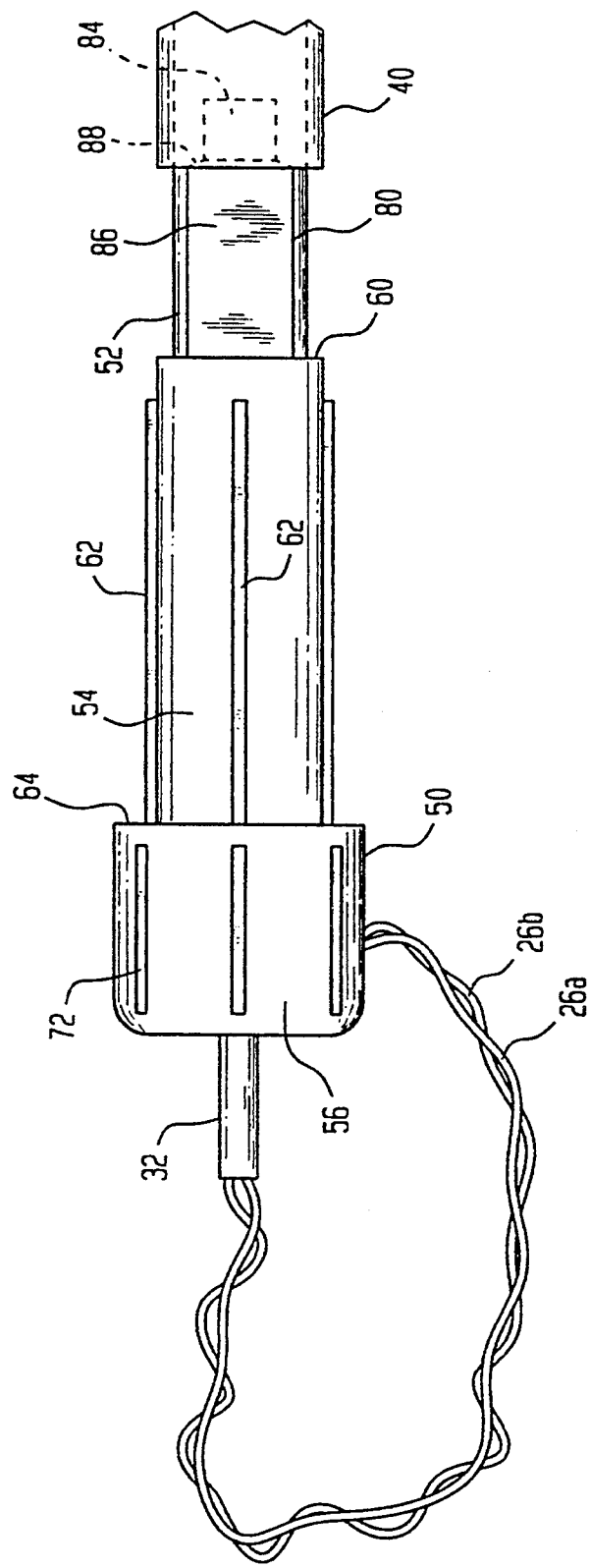

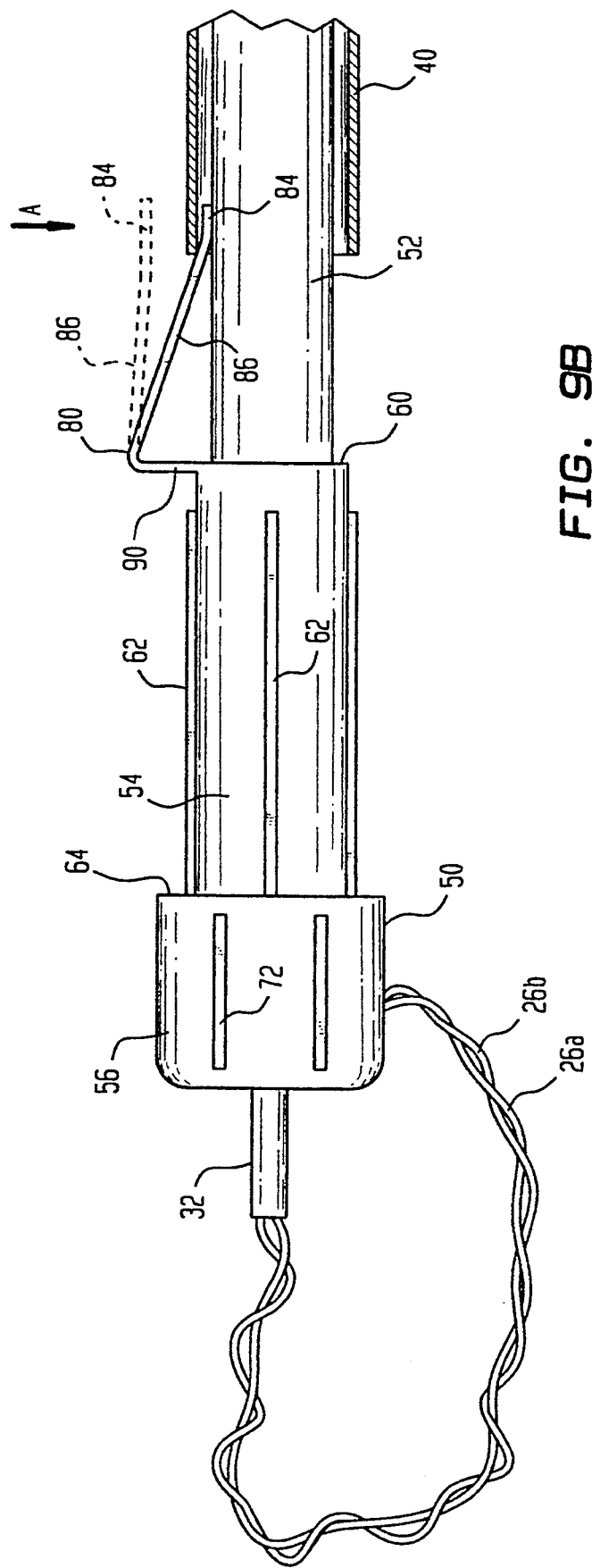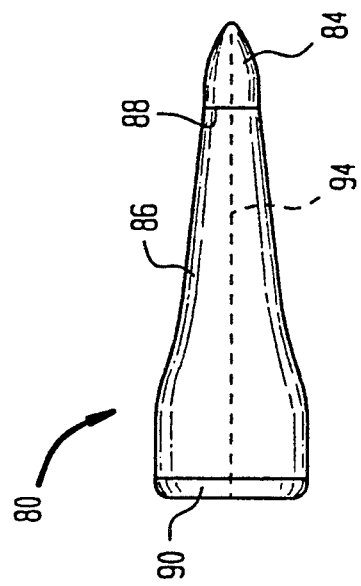

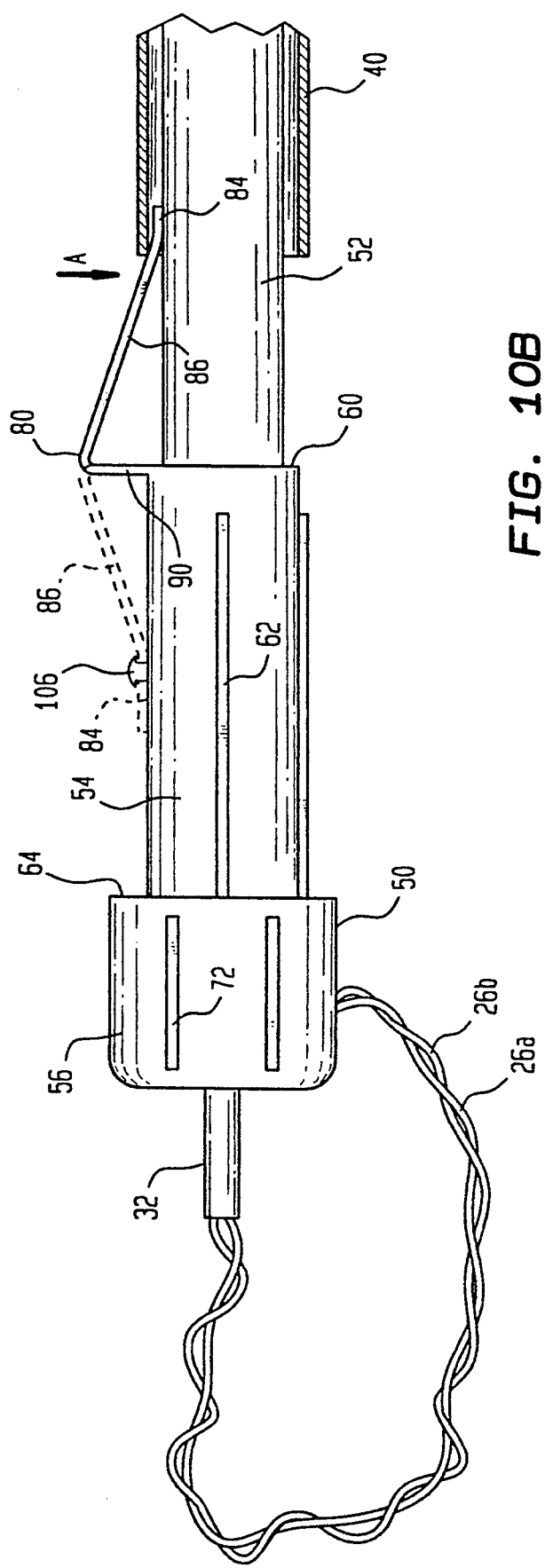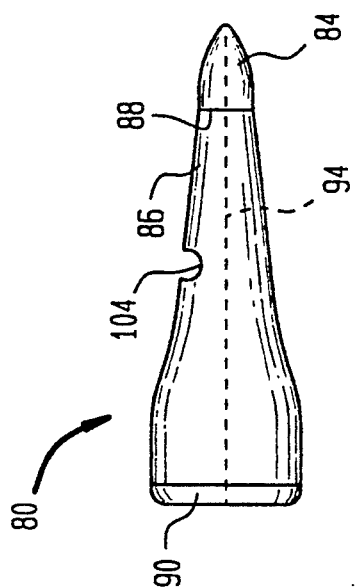

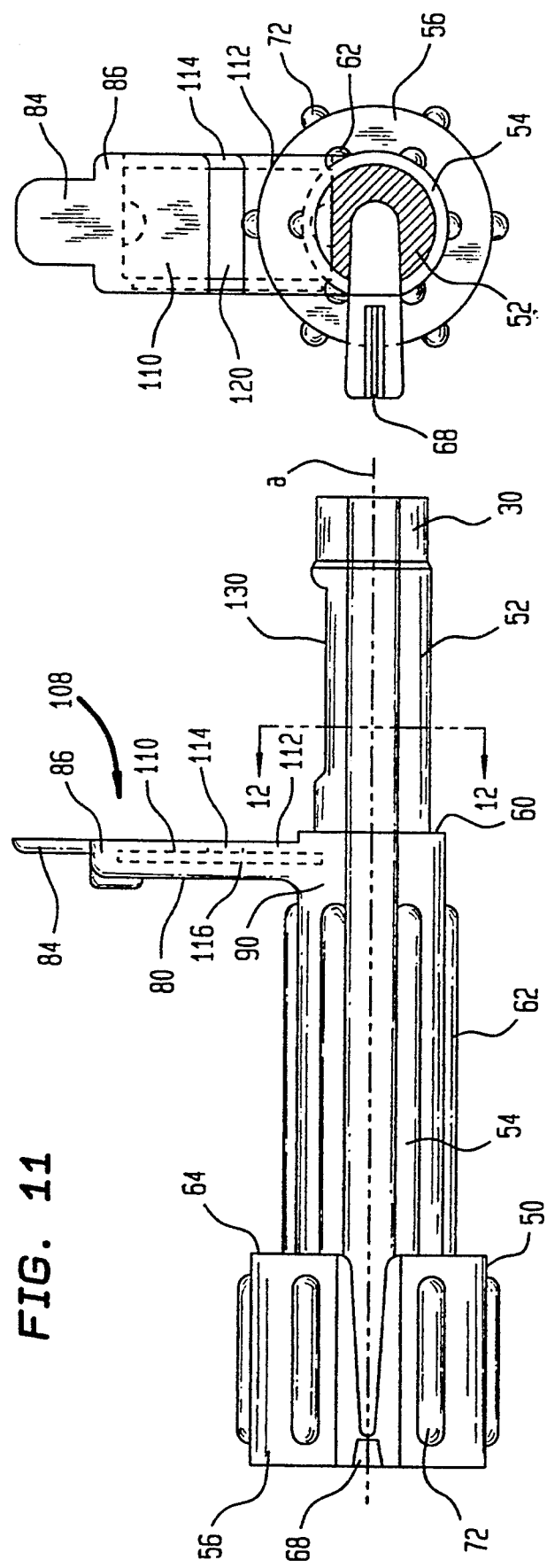
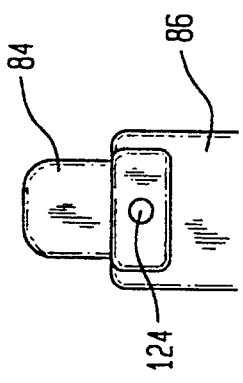
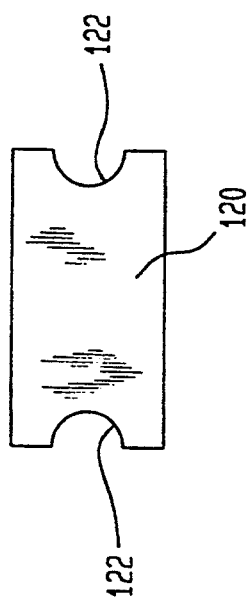

PACKAGING SYSTEM FOR A FETAL ELECTRODE

BACKGROUND OF THE INVENTION

This is a continuation in part of application Ser. No. 08/097,983, filed on Jul. 27, 1993, now abandoned, which, in turn, is a continuation in part of application Ser. No. 07/959,990, filed on Oct. 13, 1992, abandoned.

FIELD OF THE INVENTION

The present invention relates to a fetal electrode and, in particular, to a packaging system for a fetal electrode.

DESCRIPTION OF THE RELATED ART

It is desirable to monitor fetal heart rate continuously during labor and delivery in order to detect fetal distress. Devices which are external to the mother's body do not adequately isolate the fetal and maternal heartbeats. Consequently, devices which attach directly to the fetus during labor are now commonly used. U.S. Patent No. Re. 28,990, issued to Hon et al., discloses the fetal spiral electrode (FSE) assembly commonly used to monitor fetal heart rate during birth.

The fetal spiral electrode assembly includes a curved guide tube of adjustable shape for insertion of the fetal spiral electrode through the mother's cervix and into contact with the fetus during labor. A plastic tip or holder is slidably received in the guide tube. A sharp, pointed, fetal spiral electrode is mounted on the forward end of the holder for contacting the fetal epidermis.

A reference (maternal) electrode in the form of a flat fin or plate is electrically isolated from the fetal electrode and located on the rear end of the holder. A flexible drive tube with a cutout on its forward end fits inside the guide tube and engages the holder. The cutout of the drive tube engages the reference electrode in the holder to impart translation and rotation to the holder and, hence, to the fetal spiral electrode. A handle on the opposite end of the drive tube allows the user to push, pull, and rotate the drive tube.

The two electrodes are connected to separate wires, which are placed inside the drive tube. After the fetal spiral electrode is secured to the fetal epidermis, the drive tube and guide tube are removed, leaving the electrodes, the holder, and the wires in place inside the mother. The uninsulated ends of the wires opposite the electrodes are then connected to a fetal monitor.

Manual connection of the uninsulated ends of the wires is cumbersome and risks shorting the wires. If shorted, the wires cannot transmit correct signals from the fetal and reference electrodes.

Accordingly, a connector end can be added to the fetal spiral electrode assembly disclosed in the '990 patent. As taught by European Patent Application No. 91309987.5 (Publication No. 0 484 107 A1), the connector end solves the problem of manual connection of the uninsulated ends of the wires. A support plate on the body of the expectant mother receives the connector end.

The wire (typically red) connected to the fetal spiral electrode and the wire (typically green) connected to the reference electrode form a twisted wire strand which enters the connector end through a strain relief element. The red wire from the fetal spiral electrode is connected to a first, gold, terminal or ring contact; the green wire from the reference electrode is connected to a second, gold, terminal or ring contact. The terminals are electrically and physically separated by a spacer. The connector end has a forward tapered tip.

The connector end is adapted to engage the support plate, which is affixed to the mother (typically to the thigh) and provided to support the connector end. Upon insertion of the connector end into an opening of the support plate, the two ring contact terminals on the connector end click into physical and electrical contact with two corresponding barrel contacts in the support plate. Moreover, the tip of the connector end abuts a wall in the support plate to prevent over-insertion of the connector end. The support plate carries its own ground electrode.

Consequently, three electrical circuit paths are created upon connection of the connector end of the fetal spiral electrode assembly and the support plate: (a) fetal electrode to red wire to terminal to a first barrel contact to a first output terminal to the monitor; (b) reference electrode to green wire to terminal to a second barrel contact to a second output terminal to the monitor; and (c) ground electrode to a third output terminal to the monitor.

To use the fetal spiral electrode product having a connector end, the shape of the guide tube is adjusted and the guide tube is inserted through the mother's cervix and into contact with the fetus. Care must be exercised to assure that the sharp fetal spiral electrode does not extend out of the guide tube during insertion; otherwise, risk to the patient of injury and infection arises. Once the guide tube contacts the fetus (and is held against the fetus using one of the user's hands), the drive tube is advanced (using the second hand) until the fetal spiral electrode contacts the fetus.

While pressure is maintained against the fetus by the guide tube and drive tube, the drive tube is rotated, using the second hand and the handle, until the fetal spiral electrode is secured to the fetal epidermis. Typically, one full revolution suffices to secure the fetal spiral electrode. Then the drive tube and guide tube are removed, leaving the electrodes, the holder, and the wires in place inside the mother, by sliding them over the electrode wires and connector end. Finally, the connector is plugged into the leg plate.

One problem associated with the fetal spiral electrode assembly described above is the potential for the fetal spiral electrode to extend out of the guide tube before the fetal spiral electrode assembly is ready for use. If exposed, the sharp fetal spiral electrode can pierce the package, typically a paper and plastic pouch, in which the assembly is stored and transported. A person handling the electrode (or the patient) may then be harmed and sterilization of the electrode is jeopardized. In addition, the electrode itself may be damaged.

A related problem associated with the fetal spiral electrode assembly described above is the potential for the fetal spiral electrode to extend out of the guide tube during the initial stages of use. Such premature extension may injure the patient and may cause infection.

Several known devices suggest mechanisms which might prevent the fetal spiral electrode from extending out of the guide tube prematurely. For example, U.S. Pat. No. 4,321,931, issued to Neward, discusses a clip electrode having clamping portions and a carrier assembly. Before attachment to the fetus, the electrode structure is housed in the carrier with the clamping portions held apart. A plunger at the rearward end of the drive tube is held in a storage position by a guard pin, so that the drive tube is retracted into the carrier and the electrode cannot be extended. To use the device, the guard pin is aligned with a cutout, which receives the guard pin, allowing depression of the plunger.

U.S. Pat. No. 4,321,931, issued to Hon, discusses a spiral electrode attached to a holder with a helical thread on its outer surface. The helical thread engages grooves in the guide tube. The thread helps to keep the holder in a retracted position during storage. In use, a plunger is depressed, simultaneously actuating the holder forward by a predetermined distance and rotating the holder.

U.S. Pat. No. 4,934,371, issued to Malis et al., discusses a spiral electrode holder which has a cap that envelops the holder and the electrode prior to insertion of the electrode in the fetal epidermis. A bias spring keeps the cap in this position when the electrode is not in use. The cap exposes the electrode and envelops only the holder when the holder is rotated for attachment to the fetus. U.S. Pat. No. 5,012,811, issued to Malis et al., discusses a similar configuration which has a sleeve instead of a cap.

A simpler and less expensive package is desired to protect the fetal spiral electrode and to prevent injury due to accidental contact with the fetal spiral electrode.

A fetal spiral electrode manufactured by LIT Ltd. for Advanced Medical Systems, Inc., publicly available at least since February 1992, provides a detachable "spacer" to prevent the fetal spiral electrode from prematurely extending out of the guide tube. The spacer has a butterfly configuration. The wings are pressed together to separate circular legs and to create an opening between the legs. The spacer is then placed over the drive tube. Upon release of the wings, the legs close around the drive tube, holding the drive tube in the opening, and the spacer is affixed to the drive tube.

By positioning the spacer on the drive tube between the guide tube and the handle, the guide tube is prevented from sliding along the drive tube toward the handle. Consequently, the spiral electrode is prevented from extending out of the guide tube.

One disadvantage associated with using the spacer described above is that two hands are required to manipulate the spacer. The user must hold the drive tube with one hand and operated the wings of the spacer with the other hand. Thus, the user cannot hold the guide tube; hold, push, pull, or rotate the drive tube; and manipulate the spacer simultaneously. For this reason, the user must remove the spacer from the drive tube before the fetal spiral electrode assembly (including, specifically, the drive and guide tubes) is inserted into the mother. The fetal spiral electrode is free to extend out of the guide tube, therefore, after the spacer is removed and during the initial stages of use. Such premature extension may injure the patient and may cause infection. Another disadvantage of the spacer is that it constitutes an additional component which must be separately manufactured, removed, and discarded.

Additional problems associated with the fetal spiral electrode assembly described above include the potential for (1) the connector end and electrode wires to be damaged during storage and use; (2) the wires, connector end, or both to be tugged during use so that the connector end undesirably disengages the support plate; and (3) the wires to become tangled during use.

As conventionally packaged, the fetal spiral electrode assembly is placed inside a paper and plastic pouch. The paper provides a medium for written instructions and identifying information. The clear plastic permits the fetal spiral electrode assembly to be viewed. Both the paper and plastic are subject, however, to tears during handling.

The connector end and electrode wires of the fetal spiral electrode assembly are packaged conventionally in a loose state inside the paper and plastic pouch. Accordingly, they may protrude from the pouch if torn and may be physically damaged by, for example, a blow or contact with a sharp object. Additional protection from the packaging for the connector end and electrode wires during storage is desirable.

During the initial stages of use of the fetal spiral electrode assembly, the connector end and wires dangle beside the guide tube. They are subject to damage in such an unprotected position. Protection during such stages of use is desirable. During later use, the connector end is secured in the support plate. The wires are unrestricted, however, in their path from the connector end to the electrodes. Accordingly, the wires may be damaged or become tangled. Both the wires and the connector end risk tugs which might disengage the connector end from the support plate. Protection against damage, tangling, and disengagement of the connector end during such later stages of use is also desirable.

SUMMARY OF THE INVENTION

The present invention is embodied in a packaging system for a fetal spiral electrode assembly. The fetal spiral electrode assembly includes a holder which has two electrodes, each coupled to a respective electrode wire. One of the electrodes attaches to a fetus. The electrode wires extend through a drive tube which has a forward end and a rearward end. The drive tube includes at its forward end a cutout to engage the holder. A flexible guide tube, having a forward end and a rearward end, receives the drive tube. A handle is attached to the rearward end of the drive tube. The fetal spiral electrode projects from the forward end of the guide tube when the fetal spiral electrode assembly is in use.

The packaging system provides the handle of the fetal spiral electrode assembly with three sections of varying diameter to limit the extension of the fetal spiral electrode beyond the guide tube. A slot in the handle fixes the position of the electrode wires. A passage in the handle is sized to wedge the connector end of the fetal spiral electrode assembly in the passage. The passage may have a tapered diameter to facilitate insertion of the connector end. The packaging system also includes a clip with a head mounted (either detachably or integrally) to the handle of the fetal spiral electrode assembly. The clip has a tail which can be wedged between the rearward end of the guide tube and the rearward end of the drive tube when the forward section of the handle is not mounted inside the rearward end of the guide tube. The holder and the fetal spiral electrode are retracted in (and protected by) the guide tube when the handle is secured by the clip.

BRIEF DESCRIPTION OF THE DRAWINGS

FIG. 8 is a top view of the handle and clip shown in FIG. 7, illustrating the clip as inserted between the guide tube and the drive tube (the storage position for the fetal spiral electrode assembly);

FIG. 9A is a side view of the handle and clip shown in FIG. 8;

FIG. 9B is a top view of the clip shown in FIG. 9A, illustrating one shape suitable for the clip;

FIG. 10A is a side view of the handle and clip, highlighting a latching mechanism to prevent re-entry of the clip between the guide tube and drive tube;

FIG. 10B is a top view of the clip shown in FIG. 10A;

FIG. 11 is a side view of a third embodiment of the clip in accordance with the invention;

FIG. 12 is a cross-sectional view taken along the line 12—12 of FIG. 11;

FIG. 13 illustrates the leaf spring insert which is placed in the pocket of the clip shown in FIGS. 11 and 12;

FIG. 14 illustrates the ultrasonic stake which may be used to secure the leaf spring insert in the pocket of the clip;

DETAILED DESCRIPTION OF THE INVENTION

Figure 1:
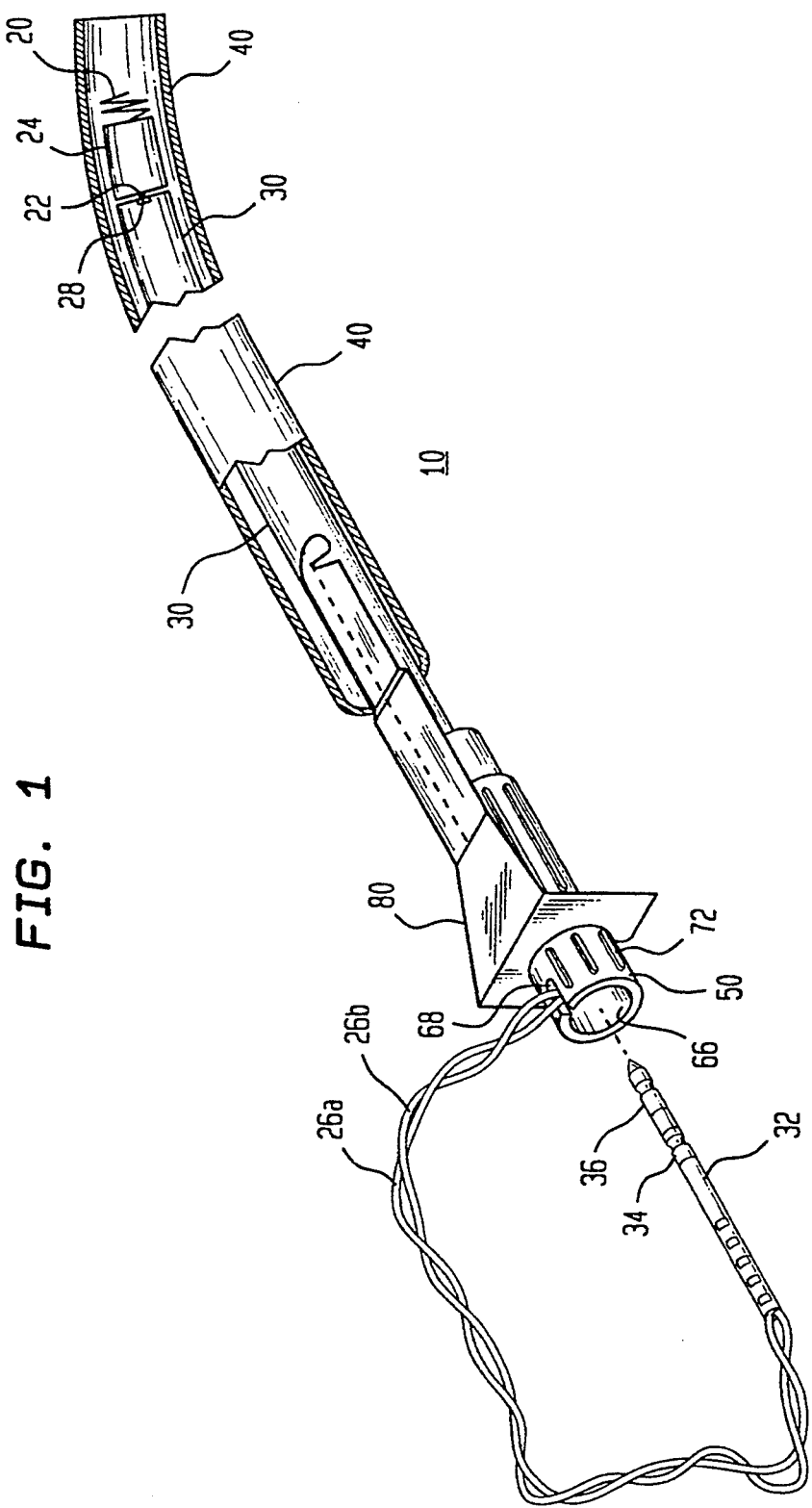
FIG. 1 is a perspective view of an exemplary fetal electrode packaging system, including a first embodiment of the clip, in accordance with the invention.

FIG. 1 shows an exemplary fetal electrode packaging system 10, for packaging an electrode assembly, in accordance with the present invention. The electrode assembly may be a conventional fetal spiral electrode assembly, which includes fetal spiral electrode 20, reference (maternal) electrode 22, holder 24, and electrode wires 26a and 26b. Holder 24 is adapted to be slidably received inside a guide tube 40. Fetal spiral electrode 20 is mounted on the forward end of holder 24. Reference electrode 22 is attached to the rearward end of holder 24 and is in the form of a plate or fin.

Electrode wires 26a and 26b (each approximately 1 mm in diameter) are separately coupled to respective electrodes 20 and 22. A flexible drive tube 30 is slidably received in guide tube 40, which has an adjustable shape. Drive tube 30 has a cutout 28 at its forward end. Electrode wires 26a and 26b extend from electrodes 20 and 22 through drive tube 30. The ends of wires 26a and 26b opposite holder 24 engage a male connector end 32 (approximately 3 mm in diameter). Connector end 32 has two ring contacts 34 and 36 which may be goldplated to resist corrosion. Ring contacts 34 and 36 have grooves to facilitate mechanical and electrical connection to mating barrel contacts in a support plate 70 (shown in FIG. 6) which mounts on the leg of an expectant mother.

To implant the spiral electrode 20 in the fetal epidermis (not shown), drive tube 30 is pushed forward in guide tube 40 with cutout 28 engaging fin-shaped reference electrode 22. Drive tube 30 and holder 24 are pushed forward, without rotation, until spiral electrode 20 contacts the fetal epidermis (not shown). By then rotating drive tube 30, while maintaining pressure against the fetus, spiral electrode 20 is secured to the fetal epidermis.

Figure 2:
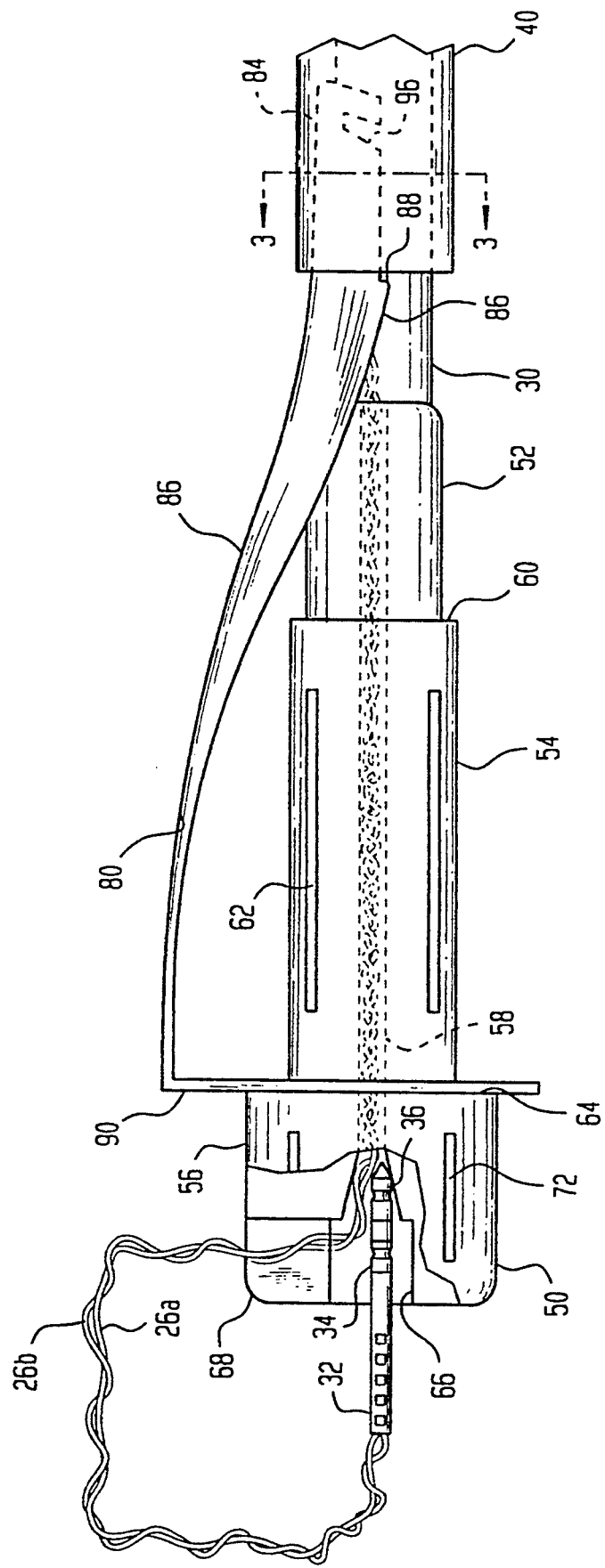
FIG. 2 is an elevation view of the handle and clip shown in FIG. 1.

A handle 50 is attached to the rearward end of drive tube 30. As shown in FIG. 2, handle 50 has three cylindrical sections: a forward section 52, a middle section 54, and a rearward section 56. A cylindrical passage 58 extends through all three sections of handle 50. Passage 58 is about 4.5 mm in diameter at its top (in rearward section 56) and may taper to a narrower diameter to ensure that connector end 32 fits snugly.

Forward section 52 of handle 50 provides a mounting end sized to be slidably received in the rearward end of guide tube 40. Middle section 54 of handle 50 has an outer diameter which is larger than the inner diameter of guide tube 40. Thus, middle section 54 provides a shoulder 60 to limit the forward movement of forward section 52 (and drive tube 30) inside guide tube 40. The respective lengths of drive tube 30, guide tube 40, and forward section 52 are selected so that spiral electrode 20 extends about 9 mm outside the forward end of guide tube 40 when forward section 52 is fully mounted inside the rearward end of guide tube 40 (such that shoulder 60 abuts the top of guide tube 40). Middle section 54 has ribs 62 to facilitate handling of drive tube 30 when attaching spiral electrode 20 to the fetus.

The rearward section 56 of handle 50 (shown partially cut away in FIG. 2) is larger in diameter than middle section 54 and forms a shoulder 64. Like middle section 54, rearward section 56 of handle 50 has ribs 72 to facilitate handling. Passage 58 ends in a counterbore 66 (about 5.5 mm in diameter) at the rearward end of rearward section 56.

A V-shaped slot 68 (as shown in FIG. 1) is provided on the outside of rearward section 56. Electrode wires 26a and 26b extend through drive tube 30 and either through (as shown in FIG. 2) or around (if a slotted drive rod rather than a drive tube is used) handle 50. Slot 68 is sized so that wires 26a and 26b can be forced upward through the wider bottom of V-shaped slot 68 into the narrower top of slot 68 to secure them when the fetal spiral electrode assembly is packaged and in the initial stages of use.

By holding wires 26a and 26b in a fixed position in slot 68, holder 24 and electrodes 20 and 22 are held against the forward end of drive tube 30. Because holder 24 cannot move away from drive tube 30 while wires 26a and 26b are secured in slot 68, engagement is assured between fin-shaped reference electrode 22 and cutout 28 of drive tube 30 during implantation of spiral electrode 20. Moreover, fixed in slot 68, wires 26a and 26b will not twist during rotation of drive tube 30 and, consequently, will not tend to untwist (and possibly unscrew spiral electrode 20 from the fetus) as drive tube 30 is removed. Slot 68 also prevents wires 26a and 26b from interfering with rotation of handle 50.

Referring again to FIG. 2, passage 58 is sized and tapered so that male connector end 32 may be wedged snugly between the wall of passage 58 and the electrode wires 26a and 26b, preventing movement of connector end 32. Male connector end 32 may be wedged snugly against the wall of passage 58 alone if electrode wires 26a and 26b pass around, rather than through, handle 50. In either case, connector end 32 is protected from damage inside passage 58. In particular, ring contacts 34 and 36 are inside passage 58, protecting them during storage and handling. Counterbore 66 facilitates insertion of connector end 32 into the relatively narrow passage 58.

A flexible clip 80 is mounted to handle 50. In a first embodiment shown in FIGS. 1–6, clip 80 is adapted to detachably mount to handle 50 at shoulder 64. The tail 84 of clip 80 is adapted to be wedged snugly between the inner diameter of guide tube 40 and the outer diameter of drive tube 30 at their rearward ends during storage and handling of the fetal spiral electrode assembly prior to use.

Clip 80 has a body 86 which is wider than tail 84. Body 86 is too wide to fit inside guide tube 40. A shoulder 88 on body 86 limits the distance by which clip 80 extends into guide tube 40. Thus, clip 80 maintains a predetermined distance between the shoulder 64 of handle rearward section 56 and the rearward end of guide tube 40 during storage. The length of clip 80 (about 82.5 mm) assures that forward section 52 of handle 50 is not mounted inside the rearward end of guide tube 40 when clip 80 is in position.

By maintaining this predetermined distance, drive tube 30 is retracted far enough inside guide tube 40 so that holder 24 and fetal spiral electrode 20 are retained in a protected position inside guide tube 40. Moreover, slot 68 secures wires 26a and 26b and holder 24 is held against the forward end of drive tube 30. Because clip 80 is wedged between drive tube 30 and guide tube 40, relative motion between the two is effectively prevented and drive tube 30 cannot slip out of guide tube 40 accidentally during handling.

Figure 4:
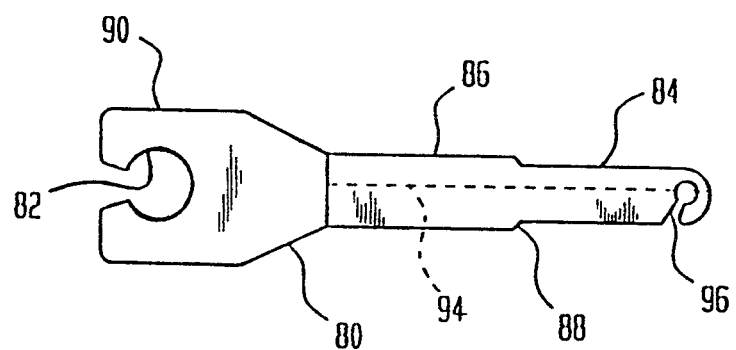
FIG. 4 is a plan view of the clip shown in FIG. 1.

Referring to FIG. 4, clip 80 is shown in greater detail. Clip 80 is formed from a single, flat, form-sustaining member (shown in FIG. 4 in its flat configuration) and can be manufactured at a cost of about 2–3 cents. Clip 80 may be formed of plastic sheet materials by a known punching process. The head 90 of clip 80 has notch 82. Notch 82 is sized (about 7.5 mm in diameter) to fit around the outer diameter of middle section 54 of handle 50. Notch 82 may be slipped over or off middle section 54 of handle 50 when attaching or removing clip 80.

Figure 3:
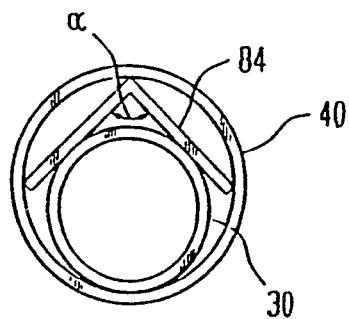
FIG. 3 is a cross-sectional view taken along line 3—3 of FIG. 2.

Head 90 is folded at first crease 92 so that head 90 is substantially perpendicular to body 86 and tail 84 of clip 80 (as shown in FIG. 2). Tail 84 of clip 80 is folded about second crease 94 so that an angle, alpha, of approximately 90° to 100° is formed at second crease 94. Angle alpha allows tail 84 to slide between drive tube 30 and guide tube 40 and to wedge drive tube 30 against the inner diameter of guide tube 40, as shown in FIG. 3.

Figure 5:
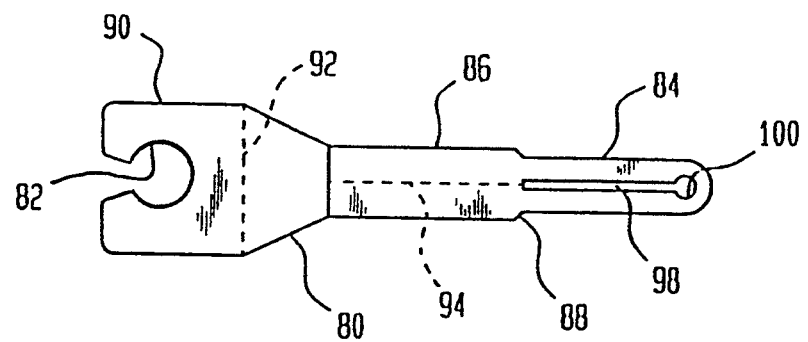
FIG. 5 is a plan view of an alternative clip design.
Figure 6:
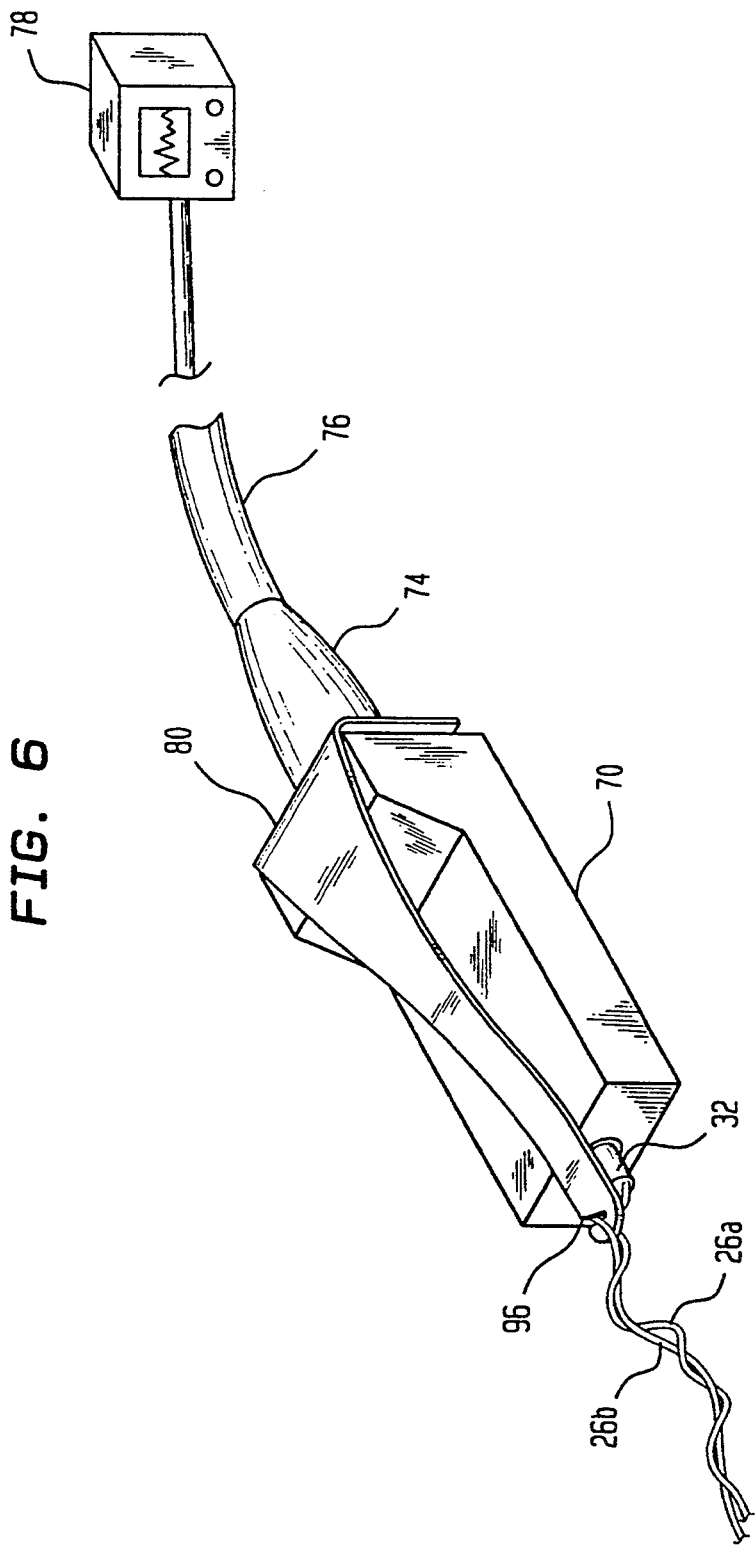
FIG. 6 depicts the clip and electrode wires shown in FIG. 1 attached to a support plate.
Figure 7:
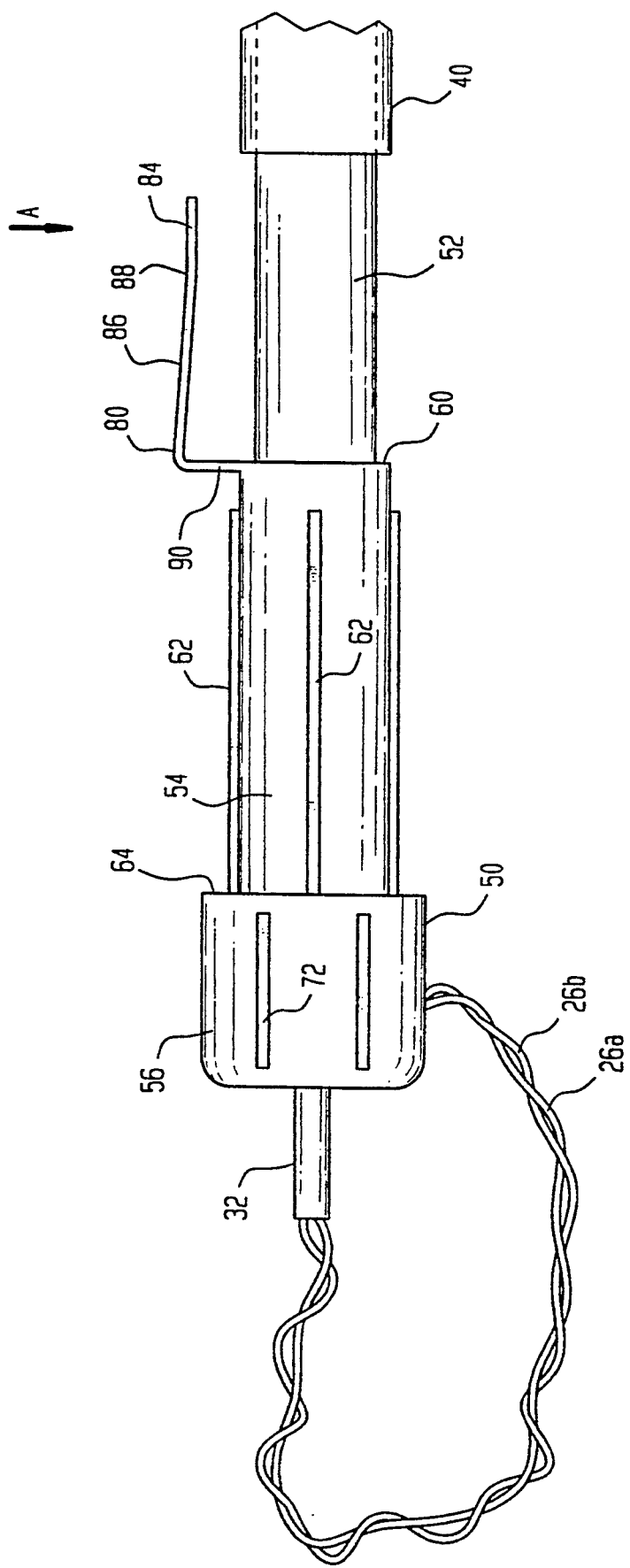
FIG. 7 is a side view of a second embodiment of the clip in accordance with the invention, illustrating the handle with the clip disengaged from between the guide tube and the drive tube.

Tail 84 of clip 80 has a hook 96 which is sized to hold wires 26a and 26b. Hook 96 is used after fetal spiral electrode 20 is attached to the fetus and connector end 32 is connected to support plate 70, as shown in FIG. 6 and discussed below. Alternatively, as shown in FIG. 5, tail 84 of clip 80 may have a slit 98 terminating in a round opening 100.

In order to use the fetal spiral electrode assembly packaged in packaging system 10 as described above, clip 80 must be removed from the electrode assembly. Removal may be accomplished in at least two different ways. First, head 90 of clip 80 may be pulled away from middle section 54 of handle 50, disengaging middle section 54 from notch 82. Then head 90 is pulled away from guide tube 40, thereby removing tail 84 from between drive tube 30 and guide tube 40. Thus, clip 80 is completely removed from the fetal spiral electrode assembly.

Alternatively, guide tube 40 may be pulled downward away from handle 50 while holding handle 50. That action will remove tail 84 from between drive tube 30 and guide tube 40, once guide tube 40 is pulled beyond the end of tail 84 of clip 80. Then body 86 or tail 84 of clip 80 may be grasped and head 90 of clip 80 may be pulled away from middle section 54 of handle 50, disengaging middle section 54 from notch 82. Thus, clip 80 is completely removed from the fetal spiral electrode assembly.

With clip 80 removed from the fetal spiral electrode assembly, fetal spiral electrode 20 can be secured to the fetal epidermis as described above. Electrode wires 26a and 26b remain in slot 68 (which prevents tangling of the wires during application and urges holder 24 against drive tube 30), and connector end 32 remains wedged into passage 58, until fetal spiral electrode 20 is attached to the fetus.

Once fetal spiral electrode 20 is secured to the fetus, connector end 32 is removed from passage 58. Electrode wires 26a and 26b are released from slot 68 and are allowed to hang freely. Drive tube 30 and guide tube 40 are then slid off electrode wires 26a and 26b and out of the mother.

As shown in FIG. 6, connector end 32 is then inserted into support plate 70. Support plate 70 is connected, via cable 76, to a monitor 78. A stress relief element 74 is provided at the junction of cable 76 and support plate 70. Insertion of connector end 32 in support plate 70 connects electrodes 20 and 22 (shown in FIG. 1) to monitor 78.

Clip 80 may now be used to secure connector end 32 in position within support plate 70. Head 90 of clip 80 is bent along first crease 92 and snapped into engagement with stress relief element 74 or cable 76 of support plate 70. Clip 80 is then placed over support plate 70 so that wires 26a and 26b can be looped through hook 96. It may be desirable to attach tail 84 (through hook 96) of clip 80 to connector end 32 instead of to wires 26a and 26b. When in position engaging support plate 70, clip 80 helps to prevent accidental release (e.g., by tugging) of connector end 32 from support plate 70 and maintains wires 26a and 26b in a position away from harm (e.g., by tangling).

For the alternative design of clip 80 shown in FIG. 5, connector end 32 can be inserted into slit 98 of tail 84 and slid downward into opening 100. Connector end 32 protrudes through opening 100 and can be inserted into support plate 70. Clip 80 is then placed over support plate 70 and head 90 is snapped into engagement with stress relief element 74 or cable 76 of support plate 70.

In a second embodiment shown in FIGS. 7–10B, flexible clip 80 is integrally mounted to handle 50 at shoulder 60. Tail 84 of clip 80 is adapted to be wedged snugly between the inner diameter of guide tube 40 and the outer diameter of forward section 52 (which transitions to drive tube 30) of handle 50 during storage and handling of the fetal spiral electrode assembly before use and during the initial stages of use before fetal spiral electrode 20 is affixed to the fetus.

Tail 84 is shown in the wedged position, the position in which the fetal spiral electrode assembly is stored before use and is held during the initial stages of use, in FIGS. 8 (top view), 9A (side view), and 10A (side view). To wedge tail 84 between guide tube 40 and drive tube 30, starting from the position shown in FIG. 7 (or the dashed position shown in FIG. 9A), tail 84 is pushed in the direction of arrow A into contact with forward section 52 of handle 50 (or drive tube 30) while guide tube 40 is pushed over tail 84.

Clip 80 has body 86 which is wider than tail 84. Body 86 is too wide to fit inside guide tube 40. Shoulder 88 on body 86 limits the distance by which clip 80 extends into guide tube 40. Thus, clip 80 maintains a predetermined distance between shoulder 64 of handle rearward section 56 and the rearward end of guide tube 40 during storage and the initial stages of use. The total length of clip 80 (about 13 mm) and the length of tail 84 (about 5 mm) assure that forward section 52 of handle 50 is not mounted completely inside the rearward end of guide tube 40 when clip 80 is wedged in position.

By maintaining this predetermined distance, drive tube 30 is retracted far enough inside guide tube 40 so that holder 24 and fetal spiral electrode 20 are retained in a protected position inside guide tube 40. Moreover, slot 68 secures wires 26a and 26b and holder 24 is held against the forward end of drive tube 30. Because clip 80 is wedged between drive tube 30 and guide tube 40, relative motion between the two is effectively prevented and drive tube 30 cannot slip out of guide tube 40 accidentally during handling.

Unlike the detachable clip 80 described above, the embodiment of clip 80 shown in FIGS. 7–10B need not be removed from the electrode assembly in order to use the fetal spiral electrode assembly packaged in packaging system 10. Rather, guide tube 40 is simply pulled away from handle 50 (and, therefore, drive tube 30) a slight distance of about 1 cm while holding handle 50. That action will remove tail 84 from between drive tube 30 and guide tube 40, once guide tube 40 is pulled beyond the end of tail 84 of clip 80, and tail 84 will spring open (in the direction opposite arrow A) into the position shown in FIG. 7 (and by the dashed lines in FIGS. 9A). Clip 80 is preferably molded from a flexible plastic material and, accordingly, has an inherent bias returning clip 80 to its initial (as molded) "open" position.

Thus, the clinician can release clip 80 without directly contacting clip 80—no additional hands are required to release clip 80. This feature of clip 80 is advantageous because, at the point during use when fetal spiral electrode 20 will be affixed to the fetal epidermis, the clinician is grasping handle 50 with one hand and guide tube 40 with the other hand. Moreover, integral clip 80 need not be removed from the electrode assembly or discarded.

With tail 84 of clip 80 removed from engagement with guide tube 40, handle 50 can be used to push drive tube 30 through guide tube 40 until the rearward end of guide tube 40 contacts shoulder 60. Then, fetal spiral electrode 20 can be secured to the fetal epidermis as described above. Clip 80 will be positioned adjacent (as shown by the dashed lines in FIG. 9A) the outer surface of guide tube 40 when guide tube 40 contacts shoulder 60. In this position, with tail 84 of clip 80 substantially parallel to guide tube 40, tail 84 can be used as a pointer to inform the user when a complete rotation of fetal spiral electrode 20 has been achieved. Such indication minimizes the risk that fetal spiral electrode 20 will penetrate insufficiently or excessively into the fetal epidermis, which would occur upon insufficient or excessive rotation, respectively, of handle 50.

It is important, once tail 84 of clip 80 is removed from between drive tube 30 and guide tube 40, that clip 80 spring into position adjacent the outer surface of guide tube 40 so that fetal spiral electrode 20 can be secured to the fetal epidermis. It is also important that, once adjacent the outer surface of guide tube 40, clip 80 (and, more specifically, tail 84) does not re-enter its initial position between drive tube 30 and guide tube 40 unless the clinician purposefully pushes clip 80 in the direction of arrow A. The features shown in FIGS. 10A and 10B and the third embodiment of clip 80 shown in FIGS. 11–16 assure that clip 80 springs into position adjacent the outer surface of guide tube 40 and does not re-enter a position between drive tube 30 and guide tube 40.

FIGS. 10A and 10B illustrate an alternative feature of packaging system 10 which entirely prevents clip 80 from assuming a position between drive tube 30 and guide tube 40. Clip 80 may be provided with an indent 104, preferably formed in body 86 of clip 80, as shown in FIG. 10B. Middle section 54 has a latch 106 formed on its surface. Once clip 80 is removed from between drive tube 30 and guide tube 40, it may be pulled or pushed in a direction opposite arrow A until indent 104 of clip 80 aligns with and engages latch 106. The engagement of indent 104 and latch 106 secures clip 80, as shown by the dashed lines in FIG. 10A, in a position away from drive tube 30 and guide tube 40.

Although the latching mechanism illustrated in FIGS. 10A and 10B prevents undesirable re-entry, the mechanism requires the user to pull or push clip 80 in a direction opposite arrow A until indent 104 of clip 80 aligns with and engages latch 106. The user does not have a free hand to push or pull clip 80 during the initial stages of use as fetal spiral electrode 20 affixed to the fetal epidermis. The third embodiment of the clip 80, illustrated in FIGS. 11–16, avoids that problem while preventing undesirable re-entry.

Figure 16:
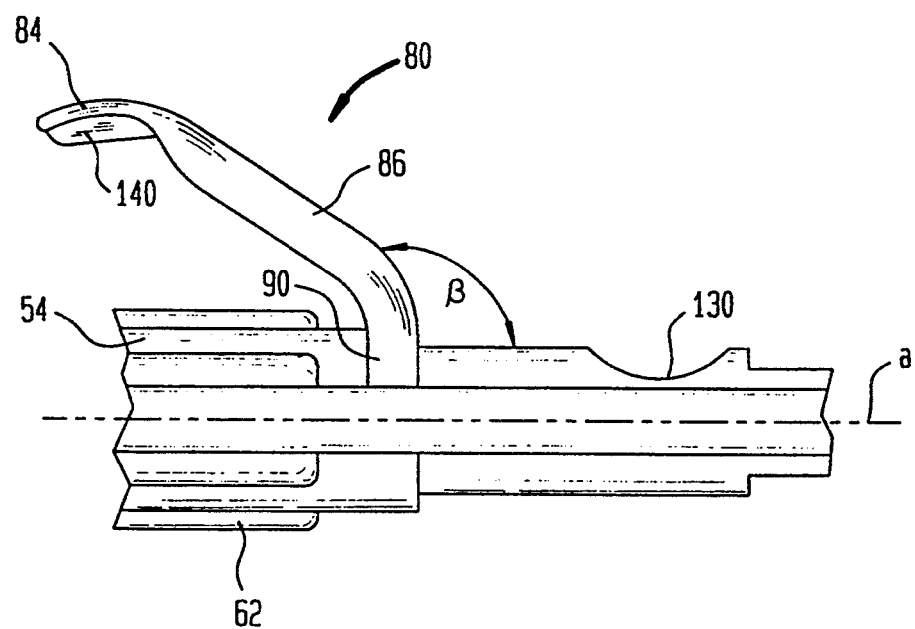
FIG. 16 is a side view of the handle and clip illustrating an alternative, molded position for the clip on the handle.

Clip 80 is preferably integral with handle 50 which, in turn, is integral with drive tube 30. These components may be molded using a relatively flexible thermoplastic material such as polyethylene. As stated above, the spring inherent in clip 80, provided by the flexibility of the plastic material of manufacture, gives clip 80 a bias which prompts clip 80 to return to its initial, molded position. Accordingly, if clip 80 is molded perpendicularly to axis "a" of handle 50 and drive tube 30 (as shown in FIG. 11), or even at an angle, beta, of greater than 90° (as shown in FIG. 16), the spring bias force inherent in clip 80 may be sufficient to prevent undesired re-entry of clip 80 between drive tube 30 and guide tube 40. That force also permits clip 80 to spring into position adjacent the outer surface of guide tube 40 during use without direct contact by the clinician.

As outlined above, clip 80 must perform four functions: (1) when wedged between drive tube 30 and guide tube 40, clip 80 must effectively retain drive tube 30 inside guide tube 40 so that holder 24 and fetal spiral electrode 20 are retained in a protected position inside guide tube 40; (2) clip 80 must be releasable from its wedged position without direct contact by the clinician; (3) once clip 80 is removed from between drive tube 30 and guide tube 40, clip 80 must spring into position adjacent the outer surface of guide tube 40 so that fetal spiral electrode 20 can be secured to the fetal epidermis; and (4) clip 80 must not re-enter a position between drive tube 30 and guide tube 40 without purposeful clinician intervention.

A molded, integral clip 80 adequately performs these functions when the electrode system is stored and used at typical, but moderate, temperatures (below about 140° F.). The mechanical properties (including stiffness) of thermoplastic materials are, however, time-temperature dependent. The thermoplastic material used to mold clip 80 may "re-set" clip 80, after initial manufacture, if subjected to a sufficiently high temperature (e.g., above 140° F.) for a prolonged time. Consequently, although clip 80 is initially molded at an angle to handle 50 with an inherent spring bias which forces clip 80 away from handle 50 and prevents re-entry between drive tube 30 and guide tube 40, clip 80 may re-set in its storage position between drive tube 30 and guide tube 40 if the fetal spiral electrode assembly is subjected to high temperature for prolonged time. As re-set, clip 80 may not spring from its wedged position into a position adjacent the outer surface of guide tube 40. Clip 80 may also tend, undesirably, to re-enter its wedged position between drive tube 30 and guide tube 40.

The third embodiment of the present invention, shown in FIGS. 11-16, allows molded, integral clip 80 to perform its four functions adequately even when the electrode system is stored and used at relatively high temperatures (above about 140° F.) for prolonged times (the electrode system has a shelf-life of at least two years). Clip 80 is provided with a pocket 108. Pocket 108 may be integrally molded with clip 80 and formed as an upper half 110 and a lower half 112 with a central gap 114. Pocket 108 defines a groove 116.

Groove 116 of pocket 108 accepts a leaf spring 120. Leaf spring 120 may be formed of spring temper stainless steel such as a 301 series stainless steel tempered to full hardness of RC 40-45. As shown in FIG. 13, leaf spring 120 has a flat, rectangular shape of dimensions 0.4 inches by 0.2 inches. The thickness of leaf spring 120 is about 0.004 inches. Other shapes, dimensions, and materials are suitable; the parameters listed are for purposes of example only. For example, leaf spring 120 might be made of half-hard 301 stainless steel to give clip 80 increased flexibility and to facilitate bending.

The example leaf spring 20 has a simple, inexpensive design which can easily be made from roll or sheet stock using a progressive die system. A pair of semicircular recesses 122 may be provided in each end of leaf spring 120 (see FIG. 13). Recesses 120 provide the symmetry required to permit assembly in either direction: end-to-end and top-to-bottom.

Leaf spring 120 may be secured in groove 116 of pocket 108 with a cylindrical, ultrasonic stake 124 (see FIG. 14). Pocket 108 is designed, with upper half 110, lower half 112, and central gap 114, to permit clip 80 to bend (as leaf spring 120 bends) uniformly without deformation. Leaf spring 120 is held in its position inside pocket 108 throughout the 180° possible range of motion for clip 80.

Leaf spring 120 gives clip 80 a spring force which is neither temperature nor time dependent. When clip 80 is released from between drive tube 30 and guide tube 40, leaf spring 120 tends to force clip 80 (assisting the spring force inherent in clip 80) to a position adjacent the outer surface of guide tube 40. Leaf spring 120 also helps to prevent clip 80 from reentering a position between drive tube 30 and guide tube 40. Thus, clip 80, provided with leaf spring 120, will perform its required functions over a wide range of environmental processing (including irradiation) and storage conditions.

As shown in FIG. 11, forward section 52 of handle 50 may be provided with a mating surface 130. Mating surface 130 is formed as an indent or recess in forward section 52 at the position where tail 84 of clip 80 contacts forward section 52 when clip 80 is placed between drive tube 30 (and handle 50) and guide tube 40. Clip 80 and mating surface 130 are designed so that when enclosed by guide tube 40 a predetermined, controlled force is required to separate guide tube 40 and drive tube 30 and, thereby, to release clip 80. A force of between about 0.5 and 1.2 pounds is suitable. Such a force allows easy separation by the user yet maintains drive tube 30 and guide tube 40 in a secure position during shipping, handling, and the initial stages of use.

Figure 15:
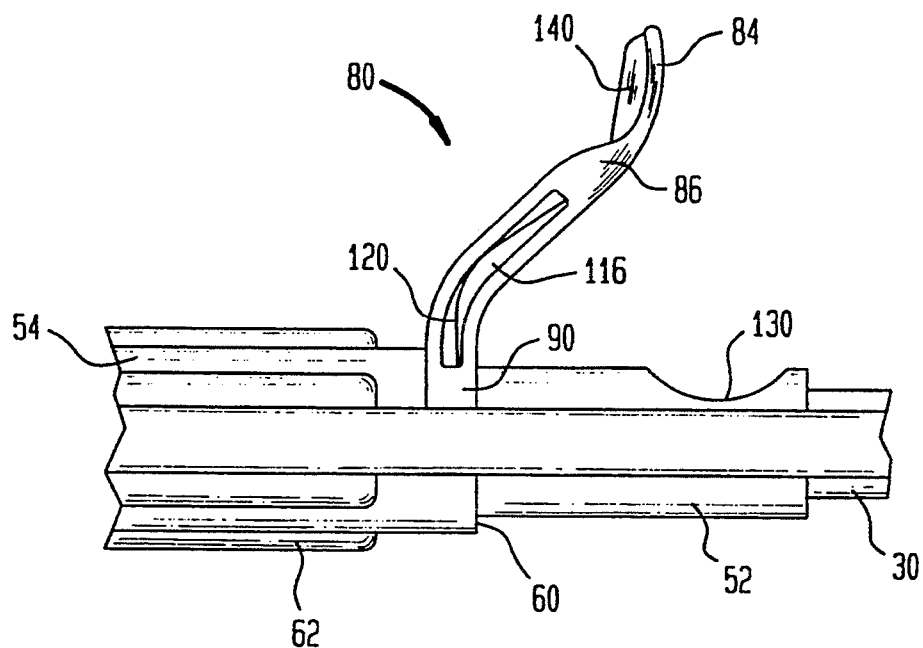
FIG. 15 is a side view of the third embodiment of the handle and clip in accordance with the invention having a curved configuration.

FIGS. 15 and 16 illustrate an alternative, curved configuration for clip 80 and mating surface 130. The curved shape of clip 80 enhances the spring force inherent in clip 80 and helps assure that clip 80 springs to a position adjacent the outer surface of guide tube 40 upon release from between drive tube 30 and guide tube 40. A ridge 140 may be molded on tail 84 of clip 80. Ridge 140 provides a surface of additional contact area between clip 80 and the inside diameter of guide tube 40 when tail 84 is in position between drive tube 30 and guide tube 40.

Many variations of the exemplary embodiments are possible. Although the description above only discusses the use of a fetal spiral electrode, handle 50 and clip 80 may be adapted for use with other electrode configurations (e.g., clamp type electrodes). Also, connector end 32 may be replaced by a female connector for use with a support plate 70 which has a male connector. To accommodate a female connector, the size of passage 58 may be modified to ensure a snug fit.

It will be understood by one skilled in the art that many variations of the embodiments described herein are contemplated. Although the invention has been described in terms of exemplary embodiments, it is contemplated that it may be practiced as outlined above with modifications within the spirit and scope of the appended claims.

What is claimed:

1. A packaging system attached to an electrode assembly which includes an electrode, a drive tube having a handle and an opposite end engaging the electrode and imparting translational and rotational motion to the electrode, and a guide tube having a forward end and in which the drive tube slides allowing the electrode to project from the forward end of the guide tube when the electrode assembly is in use, said packaging system comprising a clip having:

a tail wedging between said guide tube and said drive tube to fix the position of said drive tube in said guide tube;

a head mounted to said handle; and a body integrally connecting said head and said tail of said clip, the length of said tail, said body, and said head preselected to fix said drive tube in said guide tube with said electrode protected inside said guide tube when said electrode is not in use.

2. The packaging system in accordance with claim 1 wherein said electrode assembly includes an electrode wire connected to said electrode and said tail of said clip has a hook holding said electrode wire while said electrode is in use.

3. The packaging system in accordance with claim 2 wherein said electrode wire has at an end opposite said electrode a connector end adapted to be received by a support plate on the body of an expectant mother and said head of said clip has a notch adapted to couple with said support plate while said electrode is in use.

4. The packaging system in accordance with claim 1 wherein said clip is formed from a single flat form-sustaining member.

5. The packaging system in accordance with claim 4 wherein said clip is a folded form-sustaining member.

6. The packaging system in accordance with claim 1 wherein said clip has between said body and said tail a shoulder which abuts said guide tube and prevents insertion of said clip into said guide tube beyond said tail.

7. The packaging system in accordance with claim 1 wherein said electrode assembly includes an electrode wire connected to said electrode and said tail of said clip has a slit terminating in a round opening holding said electrode wire while said electrode is in use.

8. The packaging system as claimed in claim 1 wherein said handle has a forward section insertable into said guide tube, a middle section of larger diameter than said forward section, and a shoulder therebetween which abuts said guide tube and prevents insertion of said handle of said drive tube into said guide tube beyond said forward section.

9. The packaging system as claimed in claim 8 wherein said handle has a rearward section and a further shoulder located between said middle section and said rearward section and said head of said clip abuts said further shoulder when said head is mounted to said handle.

10. The packaging system in accordance with claim 1 wherein said electrode assembly includes an electrode wire having at an end opposite said electrode a connector end adapted to be received by a support plate on the body of an expectant mother and said handle has a passage receiving said connector end while said connector end is not attached to said support plate.

11. The packaging system in accordance with claim 10 wherein said passage has a tapered diameter.

12. The packaging system in accordance with claim 1 wherein said handle has a slot securing said electrode wire while said electrode is not in use.

13. The packaging system in accordance with claim 1 wherein said head of said clip is detachably mounted to said handle.

14. The packaging system in accordance with claim 1 wherein said head of said clip is integrally mounted to said handle.

15. The packaging system in accordance with claim 1 wherein said handle, said clip, and said drive tube are integrally molded as a single unit.

16. The packaging system in accordance with claim 15 wherein said unit is a thermoplastic material.

17. The packaging system in accordance with claim 15 wherein said handle and said drive tube are molded along a common axis and said clip is molded at an angle to said axis.

18. The packaging system in accordance with claim 17 wherein said clip has a curved configuration.

19. The packaging system in accordance with claim 1 wherein said drive tube has a mating surface and said tail of said clip engages said mating surface when said tail is wedged between said guide tube and said drive tube.

20. The packaging system in accordance with claim 1 wherein said handle has a latch and said clip has an indent, said indent adapted to engage said latch and secure said clip against said handle.

21. The packaging system in accordance with claim 1 wherein said clip has a leaf spring and a pocket defining a groove, said leaf spring disposed in said pocket.

22. The packaging system in accordance with claim 21 wherein said pocket has an upper half, a lower half, and a central gap.

23. The packaging system in accordance with claim 21 wherein said leaf spring is spring temper stainless steel.

24. The packaging system in accordance with claim 23 wherein said leaf spring has a thickness of about 0.004 inches.

25. The packaging system in accordance with claim 21 wherein said leaf spring is a flat rectangle having a recess in each of its shorter ends.

26. The packaging system in accordance with claim 21 wherein said leaf spring is fixed in said groove of said pocket by an ultrasonic stake.

27. A packaging system attached to an electrode assembly which includes an electrode, an electrode wire connected to said electrode, a connector end attached to said electrode wire at an end opposite said electrode, said connector end adapted to be received by a support plate on the body of an expectant mother, a drive tube having a forward end engaging the electrode and imparting translational and rotational motion to the electrode and a rearward end, and a guide tube having a forward end and a rearward end and in which the drive tube slides allowing the electrode to project from the forward end of the guide tube when the electrode assembly is in use, said packaging system comprising:
 a handle attached to said rearward end of said drive tube, said handle having:
 (a) a forward section which detachably mounts inside said rearward end of said guide tube, said electrode projecting from said forward end of said guide tube while said forward section is mounted inside said rearward end of said guide tube,
 (b) a middle section of larger diameter than said forward section,
 (c) a shoulder between said forward section and said middle section, said shoulder abutting said guide tube to prevent insertion of said handle of said drive tube into said guide tube beyond said forward section, and
 (d) a rearward section having a passage for receiving said connector end while said connector end is not attached to said support plate, said rearward section having a slot for securing said electrode wires while said electrode is not in use; and a clip having:
 (a) a tail wedging between said guide tube and said drive tube to fix the position of said drive tube in said guide tube, said tail of said clip having a hook holding said electrode wire while said electrode is in use,
 (b) a head detachably mounted to said handle, said head having a notch coupling with said handle when said electrode is not in use, said notch coupling with said support plate while said electrode is in use, and
 (c) a body integrally connecting said head and said tail of said clip, the length of said tail, said body, and said head preselected to fix said drive tube in said guide tube with said electrode protected inside said guide tube when said electrode is not in use.

28. A packaging system attached to an electrode assembly which includes an electrode, an electrode wire connected to said electrode, a connector end attached to said electrode wire at an end opposite said electrode, said connector end adapted to be received by a support plate on the body of an expectant mother, a drive tube having a forward end engaging the electrode and imparting translational and rotational motion to the electrode and a rearward end, and a guide tube having a forward end and a rearward end and in which the drive tube slides allowing the electrode to project from the forward end of the guide tube when the electrode assembly is in use, said packaging system comprising:

a handle attached to said rearward end of said drive tube, said handle having:
(a) a forward section which detachably mounts inside said rearward end of said guide tube, said electrode projecting from said forward end of said guide tube while said forward section is mounted inside said rearward end of said guide tube,
(b) a middle section of larger diameter than said forward section,
(c) a shoulder between said forward section and said middle section, said shoulder abutting said guide tube to prevent insertion of said handle of said drive tube into said guide tube beyond said forward section, and
(d) a rearward section having a passage for receiving said connector end while said connector end is not attached to said support plate, said rearward section having a slot for securing said electrode wires while said electrode is not in use; and a clip having:
(a) a tail wedging between said guide tube and said drive tube to fix the position of said drive tube in said guide tube,
(b) a head integrally mounted to said handle, and
(c) a body integrally connecting said head and said tail of said clip, the length of said tail, said body, and said head preselected to fix said drive tube in said guide tube with said electrode protected inside said guide tube when said electrode is not in use.

* * * * *